United States Patent
Lai et al.

(10) Patent No.: US 11,820,980 B2
(45) Date of Patent: Nov. 21, 2023

(54) METHODS AND COMPOSITIONS FOR PREPARING NUCLEIC ACID SEQUENCING LIBRARIES

(71) Applicant: Myriad Women's Health, Inc., South San Francisco, CA (US)

(72) Inventors: Henry H. Lai, South San Francisco, CA (US); Clement S. Chu, South San Francisco, CA (US)

(73) Assignee: Myriad Women's Health, Inc., South San Francisco, CA (US)

( * ) Notice: Subject to any disclaimer, the term of this patent is extended or adjusted under 35 U.S.C. 154(b) by 668 days.

(21) Appl. No.: 16/859,053

(22) Filed: Apr. 27, 2020

(65) Prior Publication Data

US 2020/0255824 A1    Aug. 13, 2020

Related U.S. Application Data

(63) Continuation of application No. PCT/US2018/057474, filed on Oct. 25, 2018.

(60) Provisional application No. 62/578,049, filed on Oct. 27, 2017.

(51) Int. Cl.
*C12N 15/10* (2006.01)
*C12N 15/11* (2006.01)
*C12Q 1/6855* (2018.01)
*C12Q 1/6874* (2018.01)

(52) U.S. Cl.
CPC .......... *C12N 15/1093* (2013.01); *C12N 15/11* (2013.01); *C12Q 1/6855* (2013.01); *C12Q 1/6874* (2013.01); *C12N 2310/32* (2013.01)

(58) Field of Classification Search
CPC .............. C12N 15/1093; C12N 15/11; C12N 2310/32; C12Q 1/6855; C12Q 1/6874
See application file for complete search history.

(56) References Cited

U.S. PATENT DOCUMENTS

| | | | |
|---|---|---|---|
| 9,745,614 B2 * | 8/2017 | Schroeder | ............ C12Q 1/6874 |
| 2013/0085083 A1 * | 4/2013 | Kamberov | ............ C12Q 1/6876 506/16 |
| 2018/0087105 A1 * | 3/2018 | Larson | ................. C12Q 1/6874 |

FOREIGN PATENT DOCUMENTS

| | | |
|---|---|---|
| WO | 2010/151842 A2 | 12/2010 |
| WO | 2014/145078 A1 | 9/2014 |
| WO | 2015/044412 A1 | 4/2015 |
| WO | 2015/134552 A1 | 9/2015 |
| WO | 2019/084245 A1 | 5/2019 |

OTHER PUBLICATIONS

Hayashi et al. "Stimulation of intermolecular ligation with E. coli DNA ligase by high concentrations of monovalent cations in polyethylene glycol solutions." Nucleic Acids Res. Nov. 25, 1985; 13(22):7979-92; doi: 10.1093/nar/13.22.7979 (Year: 1985).*
Enzymatics, Product Specifications L6090L Rev A, 2 sheets; downloaded Aug. 5, 2022 (Year: 2022).*
Enzymatics, Product Specifications P7090L Rev H, 2 sheets; downloaded Aug. 5, 2022 (Year: 2022).*
Zheng et al. "Titration-free 454 sequencing using Y adapters" Nature Protocols, (2011) vol. 6, No. 9, pp. 1367-1376 (Year: 2011).*
Alnemri, E.S., et al., Activation of Internucleosomal DNA Cleavage in Human CEM Lymphocytes by Glucocorticoid and Novobiocin, J. Biol. Chem. 265(28):17323-17333, 1990.
Altshul, S., et al., Basic Local Alignment Search Tool, J. Mol. Biol. 215:403-410, 1990.
Henikoff, S., et al., Amino acid substitution matrices from protein blocks, Proc. Natl. Acad. Sci. 89:10915-10919, 1992.
Higgins, D.G., et al., CLUSTAL: a package for performing multiple sequence alignment on a microcomputer, Gene 73:237-244, 1998.
Horhota, A., et al., Glycerol Nucleoside Triphosphates: Synthesis and Polymerase Substrate Activities, Organic Letters 8(23):5345-5347, 2006.
Karlin, S., et al., Applications and statistics for multiple high-scoring segments in molecular sequences, Proc. Natl. Acad. Sci. 90:5873-5877, 1993.
Mardis, E.R. Next-generation DNA sequencing methods, Annu Rev Genomics Hum Genet 9:387-402, 2008.
Margulies, M. et al., Genome sequencing in microfabricated high-density picolitre reactors, Nature 437:376-380, 2005.
Pearson, W.R., et al., Improved tools for biological sequence comparison, Proc. Natl. Acad. Sci. 85:2444-2448, 1988.
Richards, O.C., et al., Chemical Mechanism of Sonic, Acid, Alkaline and Enzymic Degradation of DNA, J. Mol. Biol. 11:327-340, 1965.
Soni, G.V., et al., Progress toward Ultrafast DNA Sequencing Using Solid-State Nanopores, Clin Chem 53(11):1996-2001, 2007.
Stanley, K.K., et al., Constructing Expression cDNA Libraraies Using Unphosphorylated Adaptors, Methods in Molecular Biology, vol. 4, pp. 319-328, 1988.
Agilent Technologies, https://PCR Polishing Kit, 2015, https://www.agilent.com/cs/library/usermanuals/public/200409.pdf, 9 pgs.

* cited by examiner

*Primary Examiner* — Kaijiang Zhang
(74) *Attorney, Agent, or Firm* — Foley & Lardner LLP

(57) ABSTRACT

Methods and compositions are provided for preparing DNA libraries. Enzymes, adaptors, and sample nucleic acids are provided in a single reaction mixture to facilitate library preparation.

12 Claims, 4 Drawing Sheets

METHODS AND COMPOSITIONS FOR PREPARING NUCLEIC ACID SEQUENCING LIBRARIES

CROSS-REFERENCE TO RELATED APPLICATIONS

This application is a continuation under 35 U.S.C. § 111(a) of PCT/US2018/057474, filed on Oct. 25, 2018, which claims the benefit of U.S. Provisional Application No. 62/578,049, filed Oct. 27, 2017, which is incorporated herein by reference in its entirety.

FIELD OF THE INVENTION

Methods and compositions are provided for preparing DNA libraries for downstream uses such as nucleic acid sequencing. Adaptors and reaction mixtures are provided to expedite the process of library preparation.

BACKGROUND

The advent of Next Generation Sequencing (NGS) methods generates massive amounts of nucleotide sequence information that can be used to provide sequence analysis relating to genetic information. Fundamental to NGS sequencing is library construction, which is the preparation of sample polynucleotides, RNA and/or DNA, which are to be analyzed, into a form that is compatible with the sequencing system to be used.

The process of preparation of sequencing libraries can impact significantly the quality and the output of sequencing data. Current methods for preparing nucleic acid libraries for NGS are time consuming, prone to significant sample loss, and result in low coverage of the genetic material that is being sequenced.

One current method includes adding buffer, proofreading DNA polymerase, polynucleotide kinase, and dA tailing enzymes to a nucleic acid sample and incubating at room temperature, in order to produce blunt ended and 5' phosphorylated double stranded DNA via fill-in and 3' to 5' exonuclease activities of the proofreading polymerase enzyme and the 5' phosphorylation activity of the kinase enzyme. The temperature is then increased to 65° C., to inactivate the polymerase and kinase enzymes, and to activate the dA tailing enzyme, creating a single 3' dA overhang. The temperature is then decreased back to room temperature, and additional buffer, and ligase enzyme, and dT-tailed adaptors are added to the reaction mixture. The dT-tailed adaptors anneal to the dA-tailed DNA and the strands are joined together by a ligase enzyme. The resulting library is then purified with a solid phase reversible immobilization (SPRI) bead cleanup procedure. The temperature changes and requirements for multiple addition of reagents in this procedure are inefficient. The combined incubations for the steps of this method add up to approximately 1 hour and 15 minutes.

There exists a need for improved methods for preparing polynucleotide DNA libraries, in particular methods that involve fewer steps and manipulations of the sample material.

BRIEF SUMMARY OF THE INVENTION

Methods, compositions, and kits are provided for preparing and sequencing nucleic acid libraries.

In one aspect, methods are provided for preparing a nucleic acid library. The methods include:

(a) contacting a plurality of DNA duplex fragments that include first and second nucleic acid strands with a reaction mixture that includes:
  (i) nucleic acid adaptors, wherein each adaptor includes a first nucleic acid strand with a first 5' end and a first 3' end and include a second nucleic acid strand with a second 5' end and a second 3' end, wherein each adaptor includes a double stranded region, e.g., a double stranded region that includes the first 3' end, a first single stranded region that includes the first 5' end, and a second single stranded region that includes the second 3' end, and wherein the second 3' end, i.e., the 3' end of the second single stranded region, includes a modification to prevent extension with a DNA polymerase enzyme;
  (ii) a proofreading DNA polymerase enzyme, wherein the proofreading DNA polymerase enzyme degrades 3' overhang sequences, if any, and fills in 5' overhang sequences, if any, on any present DNA species or molecules that are competent to be acted on by the enzyme, e.g., the DNA duplex fragments, and/or the nucleic acid adaptors, thereby producing blunt ended DNA duplex fragments (e.g., blunt ended DNA duplex fragments comprising first and second ends, wherein each of the first and second strands of the DNA duplex comprises a 5' terminal nucleotide), and/or adaptors with blunt ended double stranded regions comprising 5' terminal nucleotides (e.g., 5' terminal nucleotide at the second 5' end in the double stranded region of the adaptor);
  (iii) a polynucleotide kinase enzyme that phosphorylates the 5' terminal nucleotides, e.g., on the first and second strands of said DNA duplex fragments and/or on the second strands of the double stranded regions of the adaptors; and
  (iv) a ligase enzyme that joins the adaptor double stranded regions to each of the first and second blunt ends of the DNA duplex fragments, thereby producing adaptor ligated DNA duplex fragments; and (b) incubating the reaction mixture at a temperature that is appropriate for enzymatic activities of the proofreading DNA polymerase enzyme, the polynucleotide kinase enzyme, and the ligase enzyme, thereby preparing a nucleic acid library that includes adaptor ligated DNA duplex fragments.

In some embodiments, the modification to prevent extension with a DNA polymerase enzyme at the second 3' ends of the adaptors, i.e., the 3' end of the second single stranded region of the adaptor, may include, but is not limited to, a carbon spacer, a dideoxynucleotide base, or an inverted deoxynucleotide base (e.g., inverted dT).

In some embodiments, each adaptor includes a 5' overhang sequence that includes the second 5' end, and the proofreading DNA polymerase enzyme fills in the 5' overhang sequences of the double stranded regions of the adaptors, thereby producing blunt ended adaptor duplex regions with a 5' terminal nucleotide, i.e., at the second 5' end, and the polynucleotide kinase enzyme in the reaction mixture phosphorylates the 5' terminal nucleotide of the adaptor duplex.

In some embodiments, each adaptor includes a 5' overhang sequence that includes the second 5' end, and the first nucleic acid strand includes a modification to prevent degradation by an exonuclease enzyme near the first 3' end and a sequence (i.e., one or more nucleotide(s)) at the first 3' end that is not hybridized to the second nucleic acid strand. A proofreading polymerase enzyme degrades the unhybridized sequence at the 3' end back to the modification and then extends to produce a sequence that is complementary to the sequence at the 5' end of the second nucleic acid strand, thereby producing a blunt ended adaptor duplex region with a 5' terminal nucleotide, i.e., at the second 5' end, and the polynucleotide kinase enzyme in the reaction mixture phosphorylates the 5' terminal nucleotide of the adaptor duplex. For example, the modification near the first 3' end that prevents degradation by an exonuclease enzyme may include, but is not limited to, one or more nucleotides, e.g., at least two, or at least three, nucleotides with a phosphorothioate bond.

In some embodiments, the double stranded region of each adaptor is blunt ended prior to addition to the reaction mixture, with a 5' terminal nucleotide, i.e., at the second 5' end, and the polynucleotide kinase enzyme in the reaction mixture phosphorylates the 5' terminal nucleotide of the adaptor double stranded region.

In some embodiments, the double stranded region of each adaptor is blunt ended and includes a 5' terminal phosphate, prior to addition to the reaction mixture.

In some embodiments, the first 3' ends of adaptors, i.e., the 3' end that is in the adaptor duplex region, includes a modification to prevent degradation by an exonuclease enzyme. For example, the modification at the first 3' end may include, but is not limited to, one or more nucleotides, e.g., at least two, or at least three, nucleotides with a phosphorothioate bond.

In some embodiments, the first 5' ends of adaptors, i.e., the 5' end of the first single stranded region, includes a modification to prevent phosphorylation and ligation. For example, the modification at the first 5' end may include, but is not limited to, an inverted dideoxy nucleotide or a 5' carbon spacer.

In some embodiments, the adaptors include, in addition to the modification at the second 3' end to prevent extension with a DNA polymerase, both a modification at the first 3' end to prevent degradation by an exonuclease enzyme and a modification at the first 5' end to prevent phosphorylation and ligation. In an embodiment, each of the adaptors includes a 5' overhang that includes the second 5' end, and the proofreading DNA polymerase enzyme fills in the 5' overhang sequences of the double stranded regions of the adaptors, thereby producing blunt ended adaptor duplex regions, wherein the blunt ended adaptor duplex region includes a 5' terminal nucleotide, and wherein the polynucleotide kinase enzyme phosphorylates the 5' terminal nucleotide of the adaptor duplex.

In some embodiments, the adaptors include one or more of a sample index sequence, a flow cell binding sequence, a sample specific barcode sequence, and a source specific barcode sequence.

In some embodiments, the reaction mixture is incubated at a temperature of about 16° C. to about 37° C.

In some embodiments, the proofreading DNA polymerase may include, but is not limited to, T4 DNA polymerase, T7 DNA polymerase, Klenow fragment, or DNA polymerase I. In some embodiments, the polynucleotide kinase enzyme includes, but is not limited to, T4 polynucleotide kinase. In some embodiments, the ligase enzyme includes, but is not limited to, T4 DNA ligase, T3 DNA ligase, or E. coli DNA ligase.

In some embodiments, the method further includes amplifying the adaptor ligated DNA duplex fragments produced in step (b). For example, amplification may include, but is not limited to, polymerase chain reaction (PCR) or a linear amplification method.

In some embodiments, the DNA duplex fragments in step (a) include or are derived from cell-free DNA, fragmented portions of genomic DNA, or fragments including cDNA transcribed from cellular RNA of a biological sample. In some embodiments, the DNA duplex molecules include or are derived from cell-free DNA, for example, cell-free tumor DNA or cell-free fetal DNA.

In some embodiments, the method further includes obtaining or deriving the DNA duplex fragments from DNA or RNA from a biological sample prior to step (a). For example, the method may include amplifying DNA or RNA sequences from a biological tissue sample prior to step (a). For example, amplification may include, but is not limited to, PCR or a linear amplification method. The biological sample may include, for example, a biological fluid sample or a tissue sample.

In another aspect, nucleic acid libraries are provided. A nucleic acid library herein includes adaptor ligated DNA duplex fragments or amplified adaptor ligated DNA duplex fragments prepared according to any of the methods described herein.

In another aspect, methods for nucleic acid sequencing are provided. A nucleic acid sequencing method herein includes sequencing adaptor ligated DNA duplex fragments or amplified adaptor ligated DNA duplex fragments in a nucleic acid library prepared according to any of the methods described herein.

In another aspect, nucleic acid adaptors are provided. A nucleic acid adaptor herein includes:
- a first nucleic acid strand that includes a first 5' end and a first 3' end; and
- a second nucleic acid strand that includes a second 5' end and a second 3' end;
- a double stranded region, e.g., a double stranded region that includes the first 3' end;
- a first single stranded region that includes the first 5' end; and
- a second single stranded region that includes the second 3' end, wherein the second 3' end includes a modification to prevent extension with a DNA polymerase enzyme.

In some embodiments, the adaptor includes a 5' overhang that includes the second 5' end. In some embodiments, the adaptor includes a blunt ended double stranded region that includes the second 5' end with a 5' terminal phosphate or with an unphosphorylated 5' terminal nucleotide.

In some embodiments, the adaptor further includes a modification at the first 3' end to prevent degradation by an exonuclease enzyme. In some embodiments, the adaptor further includes a modification at the first 5' end to prevent phosphorylation and ligation. In some embodiments, the adaptor includes, in addition to the modification at the second 3' end to prevent extension with a DNA polymerase enzyme, both a modification at the first 3' end to prevent degradation by an exonuclease enzyme and a modification at the first 5' end to prevent phosphorylation and ligation.

In another aspect, adaptor ligated DNA duplex fragments are provided, which include a DNA duplex joined to any of the adaptors described herein. Adaptor ligated DNA duplex fragments, produced by a method as described herein are also provided.

In another aspect, kits are provided for preparing a nucleic acid library according to any of the methods described herein. In some embodiments, the kit includes adaptors according to any of the nucleic acid adaptor embodiments described herein. In some embodiments, the kit includes: (i) a proofreading DNA polymerase enzyme; (ii) a polynucleotide kinase enzyme; and (iii) a ligase enzyme, wherein the enzymes (i), (ii), and (iii) are enzymatically active at the same temperature to perform the enzymatic activities in the methods described herein for preparing a nucleic acid library.

In another aspect, reaction mixtures are provided for preparing a nucleic acid library. In some embodiments, the reaction mixture includes: (i) a proofreading DNA polymerase enzyme; (ii) a polynucleotide kinase enzyme; (iii) a ligase enzyme; (iv) a plurality of DNA duplex fragments; and (v) nucleic acid adaptors according to any of the embodiments described herein, wherein the enzymes (i), (ii), and (iii) are enzymatically active at the same temperature to perform the enzymatic activities in the methods described herein for preparing a nucleic acid library, and wherein adaptor ligated DNA duplex fragments are produced in the reaction mixture. In some embodiments, the reaction mixture is maintained at an incubation temperature at which the enzymes (i), (ii), and (iii) are enzymatically active and produce adaptor ligated DNA duplex fragments as described herein, thereby producing a nucleic acid library.

DETAILED DESCRIPTION

Figure 1A:
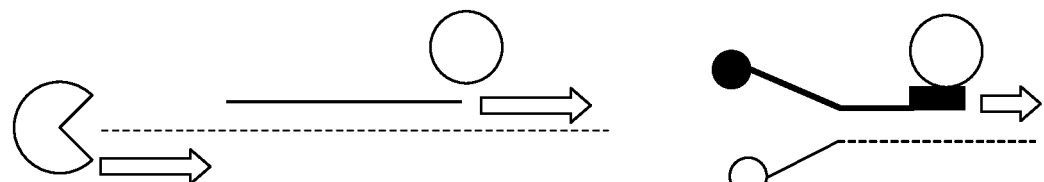
FIGS. 1A-1E schematically depict an exemplary embodiment of a method for preparation of a nucleic acid library.

Methods, compositions, and kits are provided for preparation of nucleic acid libraries. The methods described herein utilize nucleic acid adaptors that are designed to work with a combination of enzymes in a single reaction mixture, such that enzymatic reactions to prepare and join sample nucleic acids to adaptors take place at a single temperature. A plurality of adaptor ligated nucleic acids is prepared, resulting in a nucleic acid library, which may be used for downstream applications, such as nucleic acid sequencing.

Unless defined otherwise herein, all technical and scientific terms used herein have the same meaning as commonly understood by one of ordinary skill in the art to which this invention belongs. Singleton, et al., *Dictionary of Microbiology and Molecular Biology*, second ed., John Wiley and Sons, New York (1994), and Hale & Markham, *The Harper Collins Dictionary of Biology*, Harper Perennial, NY (1991) provide one of skill with a general dictionary of many of the terms used in this invention. Any methods and materials similar or equivalent to those described herein can be used in the practice or testing of the present invention.

The practice of the present invention will employ, unless otherwise indicated, conventional techniques of molecular biology (including recombinant techniques), microbiology, cell biology, and biochemistry, which are within the skill of the art. Such techniques are explained fully in the literature, for example, *Molecular Cloning: A Laboratory Manual*, second edition (Sambrook et al., 1989); *Oligonucleotide Synthesis* (M. J. Gait, ed., 1984; *Current Protocols in Molecular Biology* (F. M. Ausubel et al., eds., 1994); *PCR: The Polymerase Chain Reaction* (Mullis et al., eds., 1994); and *Gene Transfer and Expression: A Laboratory Manual* (Kriegler, 1990).

Numeric ranges provided herein are inclusive of the numbers defining the range.

The term "about" is used herein to mean plus or minus ten percent (10%) of a value. For example, "about 100" refers to any number between 90 and 110.

Unless otherwise indicated, nucleic acids are written left to right in 5' to 3' orientation; amino acid sequences are written left to right in amino to carboxy orientation, respectively.

Definitions

"A," "an" and "the" include plural references unless the context clearly dictates otherwise.

The term "adaptor" herein refers to a nucleic acid that is attached to or incorporated into a nucleic acid sequence from a sample or a nucleic acid sequence of interest to facilitate a downstream application, such as, but not limited to, nucleic acid sequencing.

In general, as used herein, a sequence element located "at the 3' end" includes the 3'-most nucleotide of the oligonucleotide, and a sequence element located "at the 5' end" includes the 5'-most nucleotide of the oligonucleotide.

An "extendible 3' end" refers an oligonucleotide with a terminal 3' nucleotide that may be extended, for example, by a polymerase enzyme, e.g., a 3' nucleotide that contains a 3' hydroxyl group.

As used herein, the term "barcode" (also termed single molecule identifier (SMI)) refers to a known nucleic acid sequence that allows some feature of a polynucleotide with which the barcode is associated to be identified. In some embodiments, the feature of the polynucleotide to be identified is the sample from which the polynucleotide is derived. In some embodiments, barcodes are about or at least about 3, 4, 5, 6, 7, 8, 9, 10, 11, 12, 13, 14, 15, or more nucleotides in length. In some embodiments, barcodes are shorter than 10, 9, 8, 7, 6, 5, or 4 nucleotides in length. In some embodiments, barcodes associated with some polynucleotides are of different lengths than barcodes associated with other polynucleotides. In general, barcodes are of sufficient length and include sequences that are sufficiently different to allow the identification of samples based on barcodes with which they are associated. In some embodiments, a barcode, and the sample source with which it is associated, can be identified accurately after the mutation, insertion, or deletion of one or more nucleotides in the barcode sequence, such as the mutation, insertion, or deletion of 1, 2, 3, 4, 5, 6, 7, 8, 9, 10, or more nucleotides. In some embodiments, each barcode in a plurality of barcodes differ from every other barcode in the plurality at least three nucleotide positions, such as at least 3, 4, 5, 6, 7, 8, 9, 10, or more nucleotide positions. A plurality of barcodes may be represented in a pool of samples, each sample including polynucleotides comprising one or more barcodes that differ from the barcodes contained in the polynucleotides derived from the other samples in the pool. Samples of polynucleotides including one or more barcodes can be pooled based on the barcode sequences to which they are joined, such that all four of the nucleotide bases A, G, C, and T are approximately evenly represented at one or more positions along each barcode in the pool (such as at 1, 2, 3, 4, 5, 6, 7, 8, or more positions, or all positions of the barcode).

A "sample barcode" refers to a nucleic acid sequence, e.g., an index sequence, that identifies a sample or source of a sample uniquely.

A "molecular barcode" refers to a nucleic acid sequence that identifies an individual nucleic acid molecule, e.g., the specific nucleic acid sequence of a molecule from a specific individual.

A "blocking group" is any modification that prevents extension of a 3' end of an oligonucleotide, such as by a polymerase, a ligase, and/or other enzymes.

The term "base pair" or "bp" as used herein refers to a partnership (i.e., hydrogen bonded pairing) of adenine (A) with thymine (T), or of cytosine (C) with guanine (G) in a double stranded DNA molecule. In some embodiments, a base pair may include A paired with Uracil (U), for example, in a DNA/RNA duplex.

A "causal genetic variant" is a genetic variant for which there is statistical, biological, and/or functional evidence of association with a disease or trait.

In general, a "complement" of a given nucleic acid sequence is a sequence that is fully complementary to and hybridizable to the given sequence. In general, a first sequence that is hybridizable to a second sequence or set of second sequences is specifically or selectively hybridizable to the second sequence or set of second sequences, such that hybridization to the second sequence or set of second sequences is preferred (e.g., thermodynamically more stable under a given set of conditions, such as stringent conditions commonly used in the art) in comparison with hybridization with non-target sequences during a hybridization reaction. Typically, hybridizable sequences share a degree of sequence complementarity over all or a portion of their respective lengths, such as 25%-100% complementarity, including at least about 25%, 30%, 35%, 40%, 45%, 50%, 55%, 60%, 65%, 70%, 75%, 80%, 85%, 90%, 91%, 92% 93%, 94%, 95%, 96%, 97%, 98%, 99%, and 100% sequence complementarity.

The term "complementary" herein refers to the broad concept of sequence complementarity in duplex regions of a single polynucleotide strand or between two polynucleotide strands between pairs of nucleotides through base-pairing. It is known that an adenine nucleotide is capable of forming specific hydrogen bonds ("base pairing") with a thymine or uracil nucleotide. Similarly, it is known that a cytosine nucleotide is capable of base pairing with a guanine nucleotide. However, in certain circumstances, hydrogen bonds may also form between other pairs of bases, e.g., between adenine and cytosine, etc. "Essentially complementary" or "substantially complementary" herein refers to sequence complementarity in duplex regions of a single polynucleotide strand or between two polynucleotide strands that is incomplete complementarity but in which stability of the duplex region is retained, for example, wherein the complementarity is less than 100% but is greater than about 90%.

The term "derived from" encompasses the terms "originated from," "obtained from," "obtainable from," "isolated from," "purified from," and "created from," and generally indicates that one specified material finds its origin in another specified material or has features that can be described with reference to the another specified material.

The term "duplex" herein refers to a region of complementarity that exists between two polynucleotide sequences. The term "duplex region" refers to the region of sequence complementarity that exists between two oligonucleotides or two portions of a single oligonucleotide.

The term "end-repaired DNA" herein refers to DNA that has been subjected to enzymatic reactions in vitro to blunt-end 5'- and/or 3'-overhangs. Blunt ends can be obtained by filling in missing bases for a strand in the 5' to 3' direction using a polymerase, and/or by removing 3'-overhangs using an exonuclease. For example, T4 polymerase and/or Klenow DNA polymerase may be used for DNA end repair.

The terms "first end" and "second end" when used in reference to a nucleic acid molecule, herein refers to ends of a linear nucleic acid molecule.

A "gene" refers to a DNA segment that is involved in producing a polypeptide and includes regions preceding and following the coding regions as well as intervening sequences (introns) between individual coding segments (exons).

"Hybridization" and "annealing" refer to a reaction in which one or more polynucleotides react to form a complex that is stabilized via hydrogen bonding between the bases of the nucleotide residues. The hydrogen bonding may occur by Watson Crick base pairing, Hoogstein binding, or in any other sequence specific manner. The complex may include two nucleic acid strands forming a duplex structure, three or more strands forming a multi-stranded complex, a single self-hybridizing strand, or any combination of these. A hybridization reaction may constitute a step in a more extensive process, such as the initiation of polymerase chain reaction (PCR), ligation reaction, sequencing reaction, or cleavage reaction, e.g., enzymatic cleavage of a polynucleotide by a ribozyme. A first nucleic acid sequence that can be stabilized via hydrogen bonding with the bases of the nucleotide residues of a second sequence is said to be "hybridizable" to the second sequence. In such a case, the second sequence can also be said to be hybridizable to the first sequence. The term "hybridized" refers to a polynucleotide in a complex that is stabilized via hydrogen bonding between the bases of the nucleotide residues.

When referring to immobilization or attachment of molecules (e.g., nucleic acids) to a solid support, the terms "immobilized" and "attached" are used interchangeably herein, and both terms are intended to encompass direct or indirect, covalent or non-covalent attachment, unless indicated otherwise. In some embodiments, covalent attachment may be preferred, but generally all that is required is that the molecules (e.g., nucleic acids) remain immobilized or attached to the support under the conditions in which it is intended to use the support, for example in nucleic acid amplification and/or sequencing applications. In some embodiments, non-covalent attachment of a nucleic acid includes hybridization of at least a portion of the nucleic acid to a complementary or substantially complementary nucleic acid sequence.

The terms "isolated," "purified," "separated," and "recovered" as used herein refer to a material (e.g., a protein, nucleic acid, or cell) that is removed from at least one component with which it is naturally associated, for example, at a concentration of at least 90% by weight, or at least 95% by weight, or at least 98% by weight of the sample in which it is contained. For example, these terms may refer to a material which is substantially or essentially free from components which normally accompany it as found in its native state, such as, for example, an intact biological system. An isolated nucleic acid molecule includes a nucleic acid molecule contained in cells that ordinarily express the nucleic acid molecule, but the nucleic acid molecule is present extrachromosomally or at a chromosomal location that is different from its natural chromosomal location.

The terms "joining" and "ligation" as used herein, with respect to two polynucleotides, such as an adaptor oligonucleotide and a sample polynucleotide, refers to the covalent attachment of two separate polynucleotides to produce a single larger polynucleotide with a contiguous backbone.

The term "library" herein refers to a collection or plurality of template nucleic acid molecules, i.e., DNA duplexes, e.g., from a biological sample. The plurality of nucleic acid molecules in a library may share common sequences at their 5' ends and/or common sequences at their 3' ends. Use of the term "library" to refer to a collection or plurality of template molecules should not be taken to imply that the templates making up the library are derived from a particular source, or that the "library" has a particular composition. By way of example, use of the term "library" should not be taken to imply that the individual templates within the library must be of different nucleotide sequence or that the templates must be related in terms of sequence and/or source.

The term "mutation" herein refers to a change introduced into a parental sequence, including, but not limited to, substitutions, insertions, and deletions (including truncations). The consequences of a mutation include, but are not limited to, the creation of a new character, property, function, phenotype or trait not found in the protein encoded by the parental sequence.

The term "Next Generation Sequencing (NGS)" herein refers to sequencing methods that allow for massively parallel sequencing of clonally amplified and of single nucleic acid molecules during which a plurality, e.g., millions, of nucleic acid fragments from a single sample or from multiple different samples are sequenced in unison. Non-limiting examples of NGS include sequencing-by-synthesis, sequencing-by-ligation, real-time sequencing, and nanopore sequencing.

The term "nucleotide" herein refers to a monomeric unit of DNA or RNA consisting of a sugar moiety (pentose), a phosphate, and a nitrogenous heterocyclic base. The base is linked to the sugar moiety via the glycosidic carbon (1' carbon of the pentose) and that combination of base and sugar is a nucleoside. When the nucleoside contains a phosphate group bonded to the 3' or 5' position of the pentose it is referred to as a nucleotide. A sequence of polymeric operatively linked nucleotides is typically referred to herein as a "base sequence," "nucleotide sequence," "polynucleotide sequence," "oligonucleotide sequence", or nucleic acid or polynucleotide "strand," and is represented herein by a formula whose left to right orientation is in the conventional direction of 5'-terminus to 3'-terminus, referring to the terminal 5' phosphate group and the terminal 3' hydroxyl group at the "5'" and "3'" ends of the polymeric sequence, respectively.

The term "nucleotide analog" herein refers to analogs of nucleoside triphosphates, of the common nucleobases: adenine, cytosine, guanine, uracil, and thymidine, e.g., (S)-Glycerol nucleoside triphosphates (gNTPs) (Horhota et al. (2006) *Organic Letters*, 8:5345-5347). Also encompassed are nucleoside tetraphosphate, nucleoside pentaphosphates and nucleoside hexaphosphates.

The term "operably linked" refers to a juxtaposition or arrangement of specified nucleic acid sequence elements that allows them to perform in concert to bring about an effect. For example, a promoter is operably linked to a coding sequence if it controls the transcription of the coding sequence.

The term "polymerase" herein refers to an enzyme that catalyzes the polymerization of nucleotides (i.e., the polymerase activity). The term polymerase encompasses DNA polymerases, RNA polymerases, and reverse transcriptases. A "DNA polymerase" catalyzes the polymerization of deoxyribonucleotides. An "RNA polymerase" catalyzes the polymerization of ribonucleotides. A "reverse transcriptase" catalyzes the polymerization of deoxyribonucleotides that are complementary to an RNA template.

The terms "polynucleotide," "nucleic acid," and "oligonucleotide" are used interchangeably. They refer to a polymeric form of nucleotides of any length, either deoxyribonucleotides or ribonucleotides, or analogs thereof. Polynucleotides may have any three-dimensional structure, and may perform any function, known or unknown, may be single- or multi-stranded (e.g., single-stranded, double-stranded, triple-helical, etc.), and may contain deoxyribonucleotides, ribonucleotides, and/or analogs or modified forms of deoxyribonucleotides or ribonucleotides, including modified nucleotides or bases or their analogs. Because the genetic code is degenerate, more than one codon may be used to encode a particular amino acid, and the present invention encompasses polynucleotides which encode a particular amino acid sequence. Any type of modified nucleotide or nucleotide analog may be used, so long as the polynucleotide retains the desired functionality under conditions of use, including modifications that increase nuclease resistance (e.g., deoxy, 2'-O-Me, phosphorothioates, etc.). Labels may also be incorporated for purposes of detection or capture, for example, radioactive or nonradioactive labels or anchors, e.g., biotin. The term polynucleotide also includes peptide nucleic acids (PNA). Polynucleotides may be naturally occurring or non-naturally occurring. Polynucleotides may contain RNA, DNA, or both, and/or modified forms and/or analogs thereof. A sequence of nucleotides may be interrupted by non-nucleotide components. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR2 ("amidate"), P(O)R, P(O)OR', CO or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need and circular portions. The following are nonlimiting examples of polynucleotides: coding or non-coding regions of a gene or gene fragment, intergenic DNA, loci (locus) defined from linkage analysis, exons, introns, messenger RNA (mRNA), transfer RNA, ribosomal RNA, short interfering RNA (siRNA), short-hairpin RNA (shRNA), micro-RNA (miRNA), small nucleolar RNA, ribozymes, cDNA, recombinant polynucleotides, branched polynucleotides, plasmids, vectors, isolated DNA of any sequence, isolated RNA of any sequence, nucleic acid probes, adaptors, and primers. A polynucleotide may include modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component, tag, reactive moiety, or binding partner. Polynucleotide sequences, when provided, are listed in the 5' to 3' direction, unless stated otherwise.

The term "primer" herein refers to an oligonucleotide, whether occurring naturally or produced synthetically, which is capable of acting as a point of initiation of nucleic acid synthesis when placed under conditions in which synthesis of a primer extension product which is complementary to a nucleic acid strand is induced, e.g., in the presence of four different nucleotide triphosphates and a polymerase enzyme, e.g., a thermostable enzyme, in an appropriate buffer ("buffer" includes pH, ionic strength, cofactors, etc.) and at a suitable temperature. The primer is preferably single-stranded for maximum efficiency in amplification, but may alternatively be double-stranded. If double-stranded, the primer is first treated to separate its strands before being used to prepare extension products. The primer may be an oligodeoxyribonucleotide. The primer must be sufficiently long to prime the synthesis of extension products in the presence of the polymerase, e.g., thermostable polymerase enzyme. The exact lengths of a primer will depend on many factors, including temperature, source of primer and use of the method. For example, depending on the complexity of the template sequence, the oligonucleotide primer typically contains 15-25 nucleotides, although it may contain more or few nucleotides. Short primer molecules generally require colder temperatures to form sufficiently stable hybrid complexes with template.

A "promoter" refers to a regulatory sequence that is involved in initiating transcription of a gene by RNA polymerase. A promoter may be an inducible promoter or a constitutive promoter. An "inducible promoter" is a promoter that is active under environmental or developmental regulatory conditions.

The term "sequencing library" herein refers to DNA that is processed for sequencing, e.g., using massively parallel methods, e.g., NGS. The DNA may optionally be amplified to obtain a population of multiple copies of processed DNA, which can be sequenced by NGS.

The term "single stranded overhang" or "overhang" is used herein to refer to a strand of a double stranded (ds) nucleic acid molecule that extends beyond the terminus of the complementary strand of the ds nucleic acid molecule, i.e., a single stranded portion that extends beyond the terminus of the duplex. The term "5' overhang" or "5' overhanging sequence" is used herein to refer to a strand of a ds nucleic acid molecule that extends beyond the 3' terminus of the complementary strand of the ds nucleic acid molecule and contains a 5' terminal nucleotide (e.g., single stranded region with a 5' phosphate group). The term "3' overhang" or "3' overhanging sequence" is used herein to refer to a strand of a ds nucleic acid molecule that extends beyond the 5' terminus of the complementary strand of the ds nucleic acid molecule and contains a 3' terminal nucleotide (e.g., a single stranded region with a 3' hydroxyl group).

A "spacer" may consist of a repeated single nucleotide (e.g., 1, 2, 3, 4, 5, 6, 7, 8, 9, 10, or more of the same nucleotide in a row), or a sequence of 2, 3, 4, 5, 6, 7, 8, 9, 10, or more nucleotides repeated 1, 2, 3, 4, 5, 6, 7, 8, 9, 10, or more times. A spacer may comprise or consist of a specific sequence, such as a sequence that does not hybridize to any target sequence in a sample. A spacer may comprise or consist of a sequence of randomly selected nucleotides.

A "subject" or "individual" refers to the source from which a biological sample is obtained, for example, but not limited to, a mammal (e.g., a human), an animal, a plant, or a microorganism (e.g., bacteria, fungi).

The phrases "substantially similar" and "substantially identical" in the context of at least two nucleic acids typically means that a polynucleotide includes a sequence that has at least about 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99%, or even 99.5% sequence identity, in comparison with a reference (e.g., wild-type) polynucleotide or polypeptide. Sequence identity may be determined using known programs such as BLAST, ALIGN, and CLUSTAL using standard parameters. (See, e.g., Altshul et al. (1990) J. Mol. Biol. 215:403-410; Henikoff et al. (1989) Proc. Natl. Acad. Sci. 89:10915; Karin et al. (1993) Proc. Natl. Acad. Sci. 90:5873; and Higgins et al. (1988) Gene 73:237). Software for performing BLAST analyses is publicly available through the National Center for Biotechnology Information. Also, databases may be searched using FASTA (Pearson et al. (1988) Proc. Natl. Acad. Sci. 85:2444-2448.) In some embodiments, substantially identical nucleic acid molecules hybridize to each other under stringent conditions (e.g., within a range of medium to high stringency).

Nucleic acid "synthesis" herein refers to any in vitro method for making a new strand of polynucleotide or elongating an existing polynucleotide (i.e., DNA or RNA) in a template dependent manner. Synthesis, according to the invention, can include amplification, which increases the number of copies of a polynucleotide template sequence with the use of a polymerase. Polynucleotide synthesis (e.g., amplification) results in the incorporation of nucleotides into a polynucleotide (e.g., extension from a primer), thereby forming a new polynucleotide molecule complementary to the polynucleotide template. The formed polynucleotide molecule and its template can be used as templates to synthesize additional polynucleotide molecules. "DNA synthesis," as used herein, includes, but is not limited to, polymerase chain reaction (PCR), and may include the use of labeled nucleotides, e.g., for probes and oligonucleotide primers, or for polynucleotide sequencing.

As used herein, the term "target polynucleotide" refers to a nucleic acid molecule or polynucleotide in a population of nucleic acid molecules having a target sequence to which one or more oligonucleotides are designed to hybridize. In some embodiments, a target sequence uniquely identifies a sequence derived from a sample, such as a particular genomic, mitochondrial, bacterial, viral, or RNA (e.g., mRNA, miRNA, primary miRNA, or pre-miRNA) sequence. In some embodiments, a target sequence is a common sequence shared by multiple different target polynucleotides, such as a common adaptor sequence joined to different target polynucleotides. "Target polynucleotide" may be used to refer to a double-stranded nucleic acid molecule that includes a target sequence on one or both strands, or a single-stranded nucleic acid molecule including a target sequence, and may be derived from any source of or process for isolating or generating nucleic acid molecules. A target polynucleotide may include one or more (e.g., 1, 2, 3, 4, 5, 6, 7, 8, 9, 10, or more) target sequences, which may be the same or different. In general, different target polynucleotides include different sequences, such as one or more different nucleotides or one or more different target sequences.

The term "template DNA molecule" herein refers to a strand of a nucleic acid from which a complementary nucleic acid strand is synthesized by a DNA polymerase, for example, in a primer extension reaction.

The term "template-dependent manner" refers to a process that involves the template dependent extension of a primer molecule (e.g., DNA synthesis by DNA polymerase). The term "template-dependent manner" typically refers to polynucleotide synthesis of RNA or DNA wherein the sequence of the newly synthesized strand of polynucleotide is dictated by the well-known rules of complementary base pairing (see, for example, Watson, J. D. et al., In: *Molecular Biology of the Gene,* 4th Ed., W. A. Benjamin, Inc., Menlo Park, Calif. (1987)).

Methods for Preparing a Nucleic Acid Library

Methods are provided for preparation of nucleic acid libraries. A plurality of nucleic acid duplex fragments is joined to adaptors in a reaction mixture that includes a proofreading DNA polymerase enzyme, a polynucleotide kinase enzyme, and a ligase enzyme.

Figure 2A:
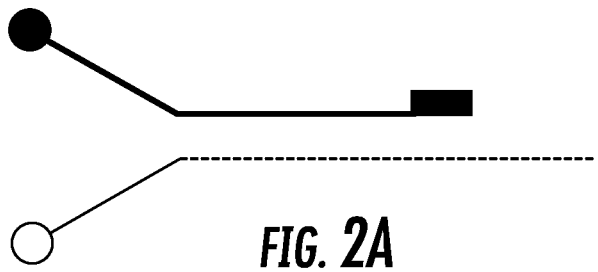
FIGS. 2A-2B depict an embodiment of an adaptor with a desired hybridized duplex region (2A) and an adaptor with undesired off-target hybridization (2B).
Figure 2B:
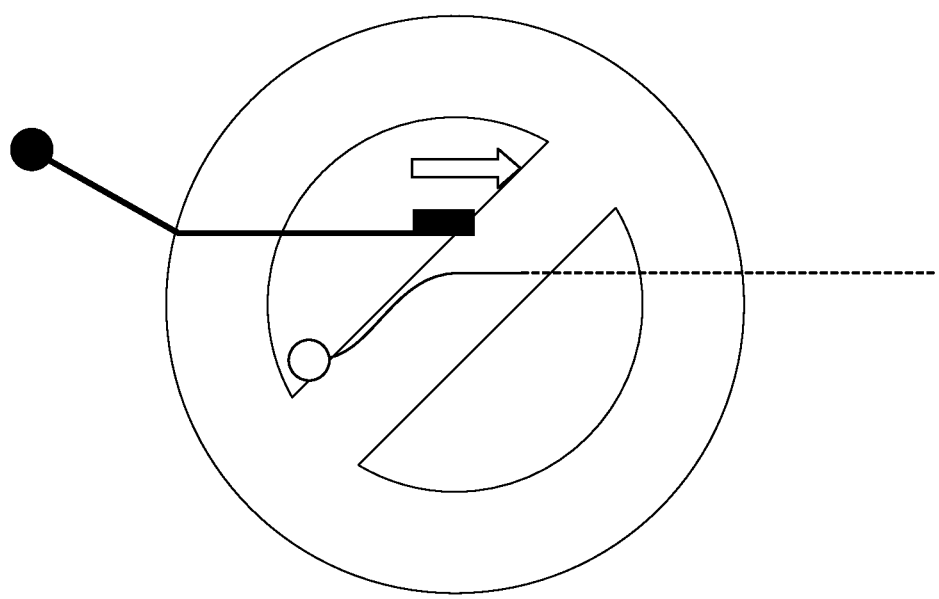

Each adaptor includes a double stranded region and two single stranded regions, a first single stranded region with 5' end and a second single stranded region with a 3' end, with a modification to prevent extension with a DNA polymerase enzyme at the 3' end of the second single stranded region. Optionally, adaptors include a 5' overhang from the double stranded region, or adaptors include a blunt ended double stranded region with or without a 5' terminal phosphate. Optionally, adaptors include a modification to prevent degradation by an exonuclease enzyme near the first 3' end and a sequence of one or more nucleotide(s) at the first 3' end that is not hybridized to the second nucleic acid strand. Optionally, adaptors include a modification at the 5' end of the first single stranded region to prevent phosphorylation and ligation, and/or a modification at the 3' end of the double stranded region to prevent exonuclease degradation. The adaptor design prevents or reduces off-target hybridization between the two strands of the adaptors, which could generate undesired adaptors and libraries. (FIGS. 2A-2B) The modifications at the 5' and 3' ends of adaptor strands prevent generation of artifacts by the enzymatic activities in the reaction mixture, preserving adaptors in the desired configuration for ligation to sample polynucleotides. (FIGS. 3A-3B) Modified 5' and 3' ends of the single stranded regions of adaptors provide protection against further enzymatic manipulation in the reaction mixture, thereby preventing formation of anomalous products.

Sample polynucleotides, adaptors, and enzymes (proofreading DNA polymerase enzyme, polynucleotide kinase enzyme, and ligase enzyme) are incubated in a single reaction mixture to produce adaptor ligated polynucleotides. In some embodiments, the temperature of the reaction mixture is about 16° C. to about 37° C. For example, the temperature may be ambient room temperature, e.g., about 20° C. to about 25° C. The reaction mixture contains other components necessary for the enzymatic activities described herein, for example, dNTPs and a suitable buffer, including necessary enzymatic co-factors, e.g., magnesium.

The reaction mixture is incubated for an appropriate amount of time for the enzymatic reactions to occur, thereby producing adaptor ligated polynucleotides. In one embodiment, the reaction mixture is incubated for about 15 minutes at room temperature. Optionally, the product library is removed from other components of the reaction mixture, for example, with a cleanup procedure, such as SPRI cleanup.

In some embodiments, the input polynucleotide molecules are amplified prior to use for preparation of a library in a method described herein. In some embodiments, the adaptor ligated polynucleotides, produced in a method herein, are amplified prior to use in a downstream application, such as, but not limited to, nucleic acid sequencing, Fragmented sample polynucleotide duplexes with overhang sequences are blunt-end polished (or "end repaired") to produce polynucleotide fragments having blunt ends, prior to being joined to adaptors, in the methods described herein.

In embodiments of the methods described herein, adaptors are joined to blunt end double-stranded DNA fragment molecules which have been modified by extension of the 3' end with one or more nucleotides followed by 5' phosphorylation. In some cases, extension of the 3' end to fill in a 5' overhang sequence, if any, and degradation of the 5' end to remove a 3' overhang sequence, if any, may be performed with a polymerase such as for example Klenow polymerase or any other suitable "proofreading" polymerases known in the art with 3'→5' exonuclease activity. In embodiments of the methods disclosed herein, sample polynucleotides having blunt ends are joined to adaptors having a blunt end. Examples of proofreading DNA polymerases that may be used in the methods described herein include, but are not limited to, T4 DNA polymerase, T7 DNA polymerase, Klenow fragment, and DNA polymerase I.

Phosphorylation of 5' ends of fragmented and blunt ended polynucleotides may be performed, for example, with T4 polynucleotide kinase.

Ligation of 5' phosphorylated polynucleotide duplex fragments and adaptors is performed with a ligase enzyme. Examples of ligase enzymes that may be used in the methods described herein include, but are not limited to, T4 DNA ligase, T3 DNA ligase, and E. coli DNA ligase.

Figure 1B:
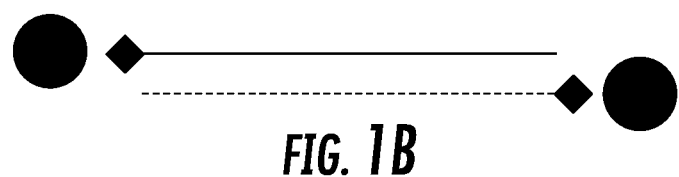
Figure 1C:
Figure 1D:
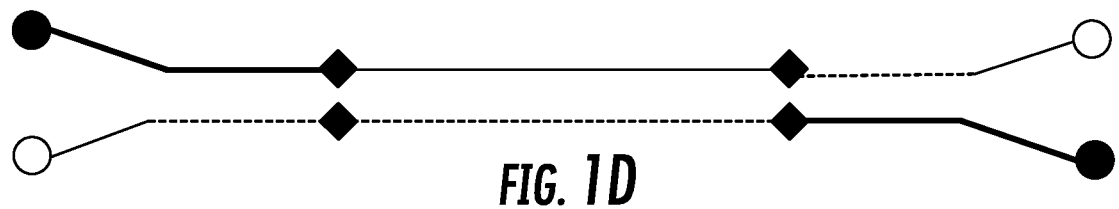
Figure 1E:

In an exemplary but non-limiting embodiment, shown schematically in FIGS. 1A-1E, the adaptors include a 5' overhang sequence from the duplex region, a modification at the 3' end of the second single stranded region to prevent extension by a DNA polymerase enzyme, a modification at the 5' end of the first single stranded region to prevent to prevent phosphorylation and ligation, and a modification at the 3' end of the double stranded region to prevent exonuclease degradation. A proofreading DNA polymerase enzyme in the reaction mixture blunts input sample polynucleotide duplex molecules and adaptors, with 5' overhang fill in and 3' overhang exonuclease cleavage (FIG. 1A). A polynucleotide kinase enzyme in the reaction mixture phosphorylates 5' ends of the adaptor duplex regions and 5' ends of the blunt ended sample polynucleotides, making adaptors and sample polynucleotides competent for ligation (FIGS. 1B-1C). A ligase enzyme in the reaction mixture joins adaptors and sample polynucleotides together, e.g., in an incubation at room temperature of about 10 to about 20, for example, about 15 minutes, producing adaptor ligated polynucleotide duplex molecules (FIG. 1D), followed by a cleanup step, resulting in a library of adaptor ligated polynucleotide molecules (FIG. 1E).

Adaptors

Polynucleotide adaptors are provided for use in the methods disclosed herein. Adaptors for use in the methods herein are partially double stranded (e.g., Y-shaped).

Adaptors as described herein include first and second nucleic acid strands. The adaptors may include a 3' nucleic acid sequence with an extendible 3' end, or an extendible 3' end is produced by enzymatic activity in the reaction mixture.

A portion of the first and second strands are capable of hybridizing, e.g., complementary, and form a duplex. A portion of each of the first and second strands forms a single stranded region of the adaptor, i.e., first and second single stranded regions, respectively. The first single stranded region includes the 5' end of the first strand, i.e., the first 5' end. The second single stranded region includes the 3' end of the second strand, i.e., the second 3' end. The 3' region of the first strand, e.g., the sequence that includes the first 3' end, forms a duplex with the 5' region of second strand, e.g., the sequence that includes the second 5' end, which may optionally include a 5' overhang sequence that includes the second 5' end.

Figure 3A:
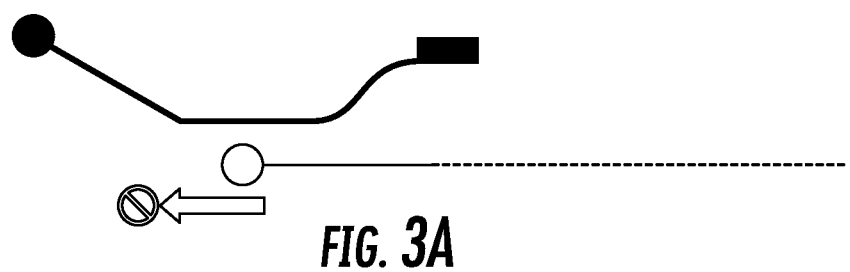
FIGS. 3A-3B depict an embodiment of an adaptor with blocking of DNA polymerase extension by a modification at the 3' end of the bottom strand single stranded region (3A) and blocking of exonuclease degradation by a modification at the 3' end of the duplex region (3B).

The second strand of each adaptor includes a modification at the second 3' end that blocks polymerase extension and exonuclease activity, preventing formation of undesired adaptor artifacts during library preparation, as shown in FIG. 3A. Nonlimiting examples of modifications at the second 3' end that block polymerase extension include a 3' carbon spacer (e.g., hexediol), a dideoxynucleotide base, or an inverted deoxyncleotide base. In one embodiment, the modification is an inverted dT base.

Optionally, the first strand of an adaptor includes a modification at the first 5' end that prevents phosphorylation and ligation, e.g., by kinase and ligase enzymes, respectively, in the library preparation reaction mixture, which would result in undesired ligation reactions. Nonlimiting examples of modifications the first 5' end that prevent phosphorylate and ligation include an inverted dideoxy nucleotide base (e.g., inverted dideoxy dT) or a 5' carbon spacer. In one embodiment, the modification is a carbon spacer.

Figure 3B:
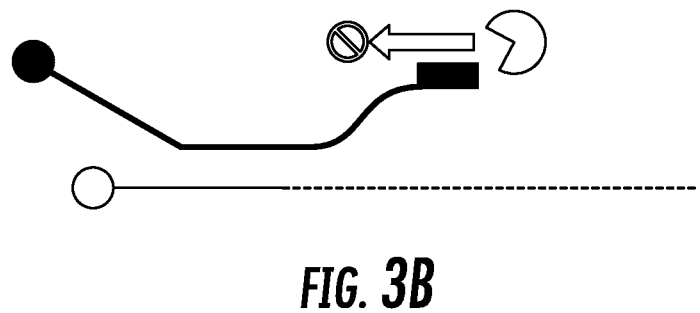

Optionally, the first strand of an adaptor includes a modification at the first 3' end that prevents exonuclease degradation which would result in undesired adaptor artifacts, as shown in FIG. 3B, e.g., by a proofreading polymerase enzyme, in the library. A nonlimiting example of a modification at the first 3' end that prevents exonuclease degradation is one or more (e.g., at least 2, for example 2, 3, 4, or more) phosphorothiate bonds, i.e., substituting a sulfur atom for a non-bridging oxygen atom in the nucleic acid phosphate backbone.

In some embodiments, an adaptor includes a modification at the second 3' end to prevent DNA polymerase extension, a modification at the first 3' end to prevent exonuclease degradation, and a modification at the first 5' end to prevent phosphorylation and ligation. In one embodiment, the adaptor includes an inverted dT at the second 3' end, a carbon spacer at the first 5' end, and one or more phosphorothioate bonds at the first 3' end.

In some embodiments, an adaptor includes a 5' overhang that extends beyond the duplex region of the adaptor and that includes the second 5' end. In other embodiments, the duplex region of an adaptor is blunt ended and includes a 5' terminal phosphate. In further embodiments, the duplex region of an adaptor is blunt ended and does not include a 5' terminal phosphate.

In some embodiments, an adaptor includes a modification to prevent degradation by an exonuclease enzyme near the first 3' end and one or more nucleotide(s) at the first 3' end that are not hybridized to the second nucleic acid strand In some embodiments, adaptors, e.g., first and/or second single stranded sequences of adaptors, include one or more nucleic acid sequence(s) that are functional in a downstream application of use. For example, an adaptor sequence may include one or more sample index sequence(s) and/or a flow binding sequence. In some embodiments, adaptors include one or more sample and/or source specific barcode sequence.

Sample Nucleic Acid Sequences

Sample nucleic acid sequences, such as specific nucleic acid sequences of interest or random nucleic acid sequences from a subject, are used in methods for preparation of a nucleic acid library as described herein. Sample nucleic acid sequences are derived from a subject, e.g., derived from a biological sample from a subject. The sample nucleic acid sequences may be double stranded or single stranded, or may include a combination of double stranded and single stranded regions.

Sample polynucleotides that can be used as the source for preparation of nucleic acid libraries as described herein include genomic cellular DNA, cell-free DNA, mitochondrial DNA, RNA, and cDNA.

In some embodiments, samples include DNA. In some embodiments, samples include genomic DNA. In some embodiments, samples include mitochondrial DNA, chloroplast DNA, plasmid DNA, bacterial artificial chromosomes, yeast artificial chromosomes, oligonucleotide tags, or combinations thereof. In some embodiments, the samples include DNA generated by amplification, such as by primer extension reactions using any suitable combination of primers and a DNA polymerase, including but not limited to polymerase chain reaction (PCR), reverse transcription, and combinations thereof. Where the template for the primer extension reaction is RNA, the product of reverse transcription is referred to as complementary DNA (cDNA). Primers useful in primer extension reactions can include sequences specific to one or more nucleic acid sequence of interest, random sequences, partially random sequences, and combinations thereof. Reaction conditions suitable for primer extension reactions are known in the art. In general, sample polynucleotides include any polynucleotide present in a sample, which may or may not include a polynucleotide sequence of interest. In some embodiments, a sample from a single individual is divided into multiple separate samples (e.g. 2, 3, 4, 5, 6, 7, 8, 9, 10, or more separate samples) that are subjected to the methods described herein independently, such as analysis in duplicate, triplicate, quadruplicate, or more.

In some embodiments, sample nucleic acid duplex molecules are provided, and are used to produce nucleic acid libraries in methods described herein. The nucleic acid duplex may be derived from a source in which it exists as double-stranded DNA, such as genomic DNA, or it may be prepared from a single-stranded nucleic acid source, such as RNA, e.g., cDNA.

Biological Sample Sources

In some embodiments, a sample that includes genomic nucleic acids to which the methods described herein may be applied may a biological sample such as a tissue sample, a biological fluid sample, or a cell sample, and processed fractions thereof. The subject from which the sample is obtained may be a mammal, for example, a human. A biological fluid sample includes, as non-limiting examples, blood, plasma, serum, sweat, tears, sputum, urine, ear flow, lymph, interstitial fluid, saliva, cerebrospinal fluid, ravages, bone marrow suspension, vaginal flow, transcervical lavage, brain fluid, ascites, milk, secretions of the respiratory, intestinal and genitourinary tracts, amniotic fluid and leukophoresis samples. In some embodiments, the source sample is a sample that is easily obtainable by non-invasive procedures, e.g., blood, plasma, serum, sweat, tears, sputum, urine, ear flow, or saliva. In some embodiments, the biological sample is a peripheral blood sample, or the plasma and serum fractions. In other embodiments, the biological sample is a swab or smear, a biopsy specimen, or a cell culture. In another embodiment, the sample is a mixture of two or more biological samples, e.g., a biological sample comprising two or more of a biological fluid sample, a tissue sample, and a cell culture sample. As used herein, the terms "blood," "plasma" and "serum" expressly encompass fractions or processed portions thereof. Similarly, where a sample is taken from a biopsy, swab, smear, etc., the "sample" expressly encompasses a processed fraction or portion derived from the biopsy, swab, smear, etc.

In some embodiments, biological samples can be obtained from sources including, but not limited to, samples from different individuals, different developmental stages of the same or different individuals, different diseased individuals (e.g., individuals with cancer or suspected of having a genetic disorder), normal individuals, samples obtained at different stages of a disease in an individual, samples obtained from an individual subjected to different treatments for a disease, samples from individuals subjected to different environmental factors, or individuals with predisposition to a pathology, individuals with exposure to a pathogen such as an infectious disease agent (e.g., HIV), and individuals who are recipients of donor cells, tissues and/or organs.

In some embodiments, the sample is a sample that includes a mixture of different source samples derived from the same or different subjects. For example, a sample can include a mixture of cells derived from two or more individuals, as is often found at crime scenes. In one embodiment, the sample is a maternal sample that is obtained from a pregnant female, for example a pregnant human woman. In this instance, the sample can be analyzed to provide a prenatal diagnosis of potential fetal disorders. Unless otherwise specified, a maternal sample includes a mixture of fetal and maternal DNA, e.g., cfDNA. In some embodiments, the maternal sample is a biological fluid sample, e.g., a blood sample. In other embodiments, the maternal sample is a purified cfDNA sample.

A sample can be an unprocessed biological sample, e.g., a whole blood sample. A source sample can be a partially processed biological sample, e.g., a blood sample that has been fractionated to provide a substantially cell-free plasma fraction. A source sample can be a biological sample containing purified nucleic acids, e.g., a sample of purified cfDNA derived from an essentially cell-free plasma sample. Processing of the samples can include freezing samples, e.g., tissue biopsy samples, fixing samples, e.g., formalin-fixing, and embedding samples, e.g., paraffin-embedding. Partial processing of samples includes sample fractionation, e.g., obtaining plasma fractions from blood samples, and other processing steps required for analyses of samples collected during routine clinical work, in the context of clinical trials, and/or scientific research. Additional processing steps can include steps for isolating and purifying sample nucleic acids. Further processing of purified samples includes, for example, steps for the requisite modification of sample nucleic acids in preparation for sequencing. Preferably, the sample is an unprocessed or a partially processed sample.

Samples can also be obtained from in vitro cultured tissues, cells, or other polynucleotide-containing sources. The cultured samples can be taken from sources including, but not limited to, cultures (e.g., tissue or cells) maintained in different media and/or conditions (e.g., pH, pressure, or temperature), maintained for different periods of time, and/or treated with different factors or reagents (e.g., a drug candidate, or a modulator), or mixed cultures of different types of tissue or cells.

Biological samples can be obtained from a variety of subjects, including but not limited to, mammals, e.g., humans, and other organisms, including, plants, or cells from the subjects, or microorganisms (e.g., bacteria, fungi).

Biological samples from which the sample polynucleotides are derived can include multiple samples from the same individual, samples from different individuals, or combinations thereof. In some embodiments, a sample includes a plurality of polynucleotides from a single individual. In some embodiments, a sample includes a plurality of polynucleotides from two or more individuals. An individual is any organism or portion thereof from which sample polynucleotides can be derived, non-limiting examples of which include plants, animals, fungi, protists, monerans, viruses, mitochondria, and chloroplasts.

Sample polynucleotides can be isolated from a subject, such as a cell sample, tissue sample, fluid sample, or organ sample derived therefrom (or cell cultures derived from any of these), including, for example, cultured cell lines, biopsy, blood sample, cheek swab, or fluid sample containing a cell (e.g., saliva). The subject may be an animal, including but not limited to, a cow, a pig, a mouse, a rat, a chicken, a cat, a dog, etc., and in some embodiments is a mammal, such as a human.

Preparation of Sample Nucleic Acids

Methods for the extraction and purification of nucleic acids are well known in the art. For example, nucleic acids can be purified by organic extraction with phenol, phenol/chloroform/isoamyl alcohol, or similar formulations, including TRIzol™ and TRI Reagent®. Other non-limiting examples of extraction techniques include: (1) organic extraction followed by ethanol precipitation, e.g., using a phenol/chloroform organic reagent, with or without the use of an automated nucleic acid extractor; (2) stationary phase adsorption; and (3) salt-induced nucleic acid precipitation methods, such precipitation methods being typically referred to as "salting-out" methods.

Another example of nucleic acid isolation and/or purification includes the use of magnetic particles to which nucleic acids can specifically or non-specifically bind, followed by isolation of the beads using a magnet, and washing and eluting the nucleic acids from the beads. In some embodiments, the above isolation methods may be preceded by an enzyme digestion step to help eliminate unwanted protein from the sample, e.g., digestion with proteinase K, or other like proteases. If desired, RNase inhibitors may be added to the lysis buffer.

For certain cell or sample types, it may be desirable to add a protein denaturation/digestion step to the protocol. Purification methods may be directed to isolate DNA, RNA, or both. When both DNA and RNA are isolated together during or subsequent to an extraction procedure, further steps may be employed to purify one or both separately from the other. Sub-fractions of extracted nucleic acids can also be generated, for example, purification by size, sequence, or other physical or chemical characteristic.

In addition to an initial nucleic acid isolation step, purification of nucleic acids can be performed after preparation of a nucleic acid library in a method described herein, such as to remove excess or unwanted reagents, reactants, or products. Methods for determining the amount and/or purity of nucleic acids in a sample are known in the art, and include absorbance (e.g., absorbance of light at 260 nm, 280 nm, and a ratio of these) and detection of a label (e.g., fluorescent dyes and intercalating agents, such as SYBR green, SYBR blue, DAPI, propidium iodine, Hoechst stain, SYBR gold, ethidium bromide).

In some embodiments, sample nucleic acid molecules are fragmented, e.g., fragmentation of cellular genomic DNA. Fragmentation of polynucleotide molecules by mechanical means cleaves the DNA backbone at C—O, P—O and C—C bonds, resulting in a heterogeneous mix of blunt and 3'- and 5'-overhanging ends with broken C—O, P—O and/C—C bonds (Alnemri and Litwack (1990) *J Biol Chem* 265: 17323-17333; Richards and Boyer (1965) *J Mol Biol* 11:327-340), which may need to be repaired for subsequent method steps. Therefore, fragmentation of polynucleotides, e.g., cellular genomic DNA, may be required. Alternatively, fragmentation of cfDNA, which exists as fragments of <300 bases, may not necessary.

In some embodiments, polynucleotides are fragmented into a population of fragmented polynucleotides of one or more specific size range(s). In some embodiments, the amount of sample polynucleotides subjected to fragmentation is about, less than about, or more than about 50 ng, 100 ng, 200 ng, 300 ng, 400 ng, 500 ng, 600 ng, 700 ng, 800 ng, 900 ng, 1000 ng, 1500 ng, 2000 ng, 2500 ng, 5000 ng, 1 µg, 10 µg, or more. In some embodiments, fragments are generated from about, less than about, or more than about 1, 10, 100, 1000, 10,000, 100,000, 300,000, 500,000, or more genome-equivalents of starting DNA. In some embodiments, the fragments have an average or median length from about 10 to about 10,000 nucleotides (e.g., base pairs). In some embodiments, the fragments have an average or median length from about 50 to about 2,000 nucleotides (e.g., base pairs). In some embodiments, the fragments have an average or median length of about, less than about, more than about, or about 100 to about 2500, about 200 to about 1000, about 10 to about 800, about 10 to about 500, about 50 to about 500, about 50 to about 250, or about 50 to about 150 nucleotides (e.g., base pairs). In some embodiments, the fragments have an average or median length of about 300 to about 800 nucleotides (e.g., base pairs). In some embodiments, the fragments have an average or median length of about, less than about, or more than about 200, 300, 500, 600, 800, 1000, 1500 or more nucleotides (e.g., base pairs).

Fragmentation may be accomplished by methods known in the art, including chemical, enzymatic, and mechanical fragmentation. In some embodiments, the fragmentation is accomplished mechanically, including subjecting sample polynucleotides to acoustic sonication. In some embodiments, the fragmentation includes treating the sample polynucleotides with one or more enzymes under conditions suitable for the one or more enzymes to generate double-stranded nucleic acid breaks. Examples of enzymes useful in the generation of polynucleotide fragments include sequence specific and non-sequence specific nucleases. Non-limiting examples of nucleases include DNase I, Fragmentase®, restriction endonucleases, variants thereof, and combinations thereof. For example, digestion with DNase I can induce random double-stranded breaks in DNA in the absence of $Mg^{2+}$ and in the presence of $Mn^{2+}$.

In some embodiments, fragmentation includes treating the sample polynucleotides with one or more restriction endonucleases. Fragmentation can produce fragments having 5' overhangs, 3' overhangs, blunt ends, or a combination thereof. In some embodiments, such as when fragmentation includes the use of one or more restriction endonucleases, cleavage of sample polynucleotides leaves overhangs having a predictable sequence.

In some embodiments, the method includes the step of size selecting the fragments via standard methods such as column purification or isolation from an agarose gel. In some embodiments, the method includes determining the average and/or median fragment length after fragmentation. In some embodiments, samples having an average and/or median fragment length above a desired threshold are again subjected to fragmentation. In some embodiments, samples having an average and/or median fragment length below a desired threshold are discarded.

Variant Sequences

In some embodiments, the sample nucleic acid includes a variant sequence, e.g., a causal genetic variant or an aneuploidy. A single causal genetic variant can be associated with more than one disease or trait. In some embodiments, a causal genetic variant can be associated with a Mendelian trait, a non-Mendelian trait, or both. Causal genetic variants can manifest as variations in a polynucleotide, such as at least about 1, 2, 3, 4, 5, 6, 7, 8, 9, 10, 20, 50, or more sequence differences (such as between a polynucleotide including the causal genetic variant and a polynucleotide lacking the causal genetic variant at the same relative genomic position).

Non-limiting examples of types of causal genetic variants include single nucleotide polymorphisms (SNP), deletion/insertion polymorphisms (DIP), copy number variants (CNV), short tandem repeats (STR), restriction fragment length polymorphisms (RFLP), simple sequence repeats (SSR), variable number of tandem repeats (VNTR), randomly amplified polymorphic DNA (RAPD), amplified fragment length polymorphisms (AFLP), inter-retrotransposon amplified polymorphisms (IRAP), long and short interspersed elements (LINE/SINE), long tandem repeats (LTR), mobile elements, retrotransposon microsatellite amplified polymorphisms, retrotransposon-based insertion polymorphisms, sequence specific amplified polymorphism, and heritable epigenetic modification (for example, DNA methylation).

In some embodiments, the sample nucleic acid sequence includes a non-subject sequence. In general, a non-subject sequence corresponds to a polynucleotide derived from an organism other than the individual being tested, such as DNA or RNA from bacteria, archaea, viruses, protists, fungi, or other organism. A non-subject sequence may be indicative of the identity of an organism or class of organisms, and may further be indicative of a disease state, such as infection. An example of non-subject sequences useful in identifying an organism include, without limitation, ribosomal RNA (rRNA) sequences, such as 16 s rRNA sequences (see, e.g., WO2010/151842). In some embodiments, non-subject sequences are analyzed instead of, or separately from causal genetic variants. In some embodiments, causal genetic variants and non-subject sequences are analyzed in parallel, such as in the same sample and/or in the same report.

Nucleic Acid Libraries

Nucleic acid libraries are provided. The libraries include adaptor ligated nucleic acids, produced in a method as described herein. A library may include adaptors ligated to nucleic acids or amplified nucleic acids, for example from a biological sample or source as described herein, supra. For example, the nucleic acids may include cell-free DNA, fragmented portions of genomic DNA, or cDNA transcribed from cellular RNA, or amplified nucleic acid products thereof.

The adaptors may be of any configuration described herein, supra. For example, a sample nucleic acid duplex may be ligated at each end to the duplex region of an adaptor. The ligated adaptors include a single stranded region with a 3' end modified to prevent extension by a DNA polymerase enzyme, and optionally further include a single stranded region with a 5' end modified to prevent phosphorylation and ligation.

Nucleic Acid Sequencing

Methods for sequencing nucleic acids are provided. The methods include adaptor ligated nucleic acids, produced in a method as described herein, e.g., provided as a nucleic acid library.

In one embodiment, Illumina sequencers are used for sequencing of the adaptor ligated nucleic acids. Illumina produces a widely used family of platforms. The technology was introduced in 2006 (www.illumina.com) and was quickly embraced by many researchers because a larger amount of data could be generated in a more cost-effective manner. Illumina sequencing is a sequencing-by-synthesis method, which differs from "454" sequencing methods, described infra, in two major ways: (1) it uses a flow cell with a field of oligo's attached, instead of a chip containing individual microwells with beads, and (2) it does not involve pyrosequencing, but rather reversible dye terminators.

In another embodiment, a dye-termination sequencing approach is used for sequencing of the adaptor ligated nucleic acids. Dye-termination resembles the "traditional" Sanger sequencing. It is different from Sanger, however, in that the dye terminators are reversible, so they are removed after each imaging cycle to make way for the next reversible dye-terminated nucleotide. Sequencing preparation begins with lengths of DNA that have specific adaptors on either end being washed over a flow cell filled with specific oligonucleotides that hybridize to the ends of the fragments. Each fragment is then replicated to make a cluster of identical fragments. Reversible dye-terminator nucleotides are then washed over the flow cell and given time to attach; the excess nucleotides are washed away, the flow cell is imaged, and the terminators are reversed so that the process can repeat and nucleotides can continue to be added in subsequent cycles.

In another embodiment, 454 sequencing (http://www.454.com/) (e.g., as described in Margulies, M. et al. (2005) *Nature* 437:376-380) is used for sequencing of the adaptor ligated nucleic acids. The overall approach for 454 is pyrosequencing based. The sequencing preparation begins with lengths of DNA (e.g., amplicons or nebulized genomic/metagenomic DNA) that have adaptors on either end, created by using PCR primers with adaptor sequences or by ligation; these are fixed to tiny beads (ideally, one bead will have one DNA fragment) that are suspended in a water-in-oil emulsion. An emulsion PCR step is then performed to make multiple copies of each DNA fragment, resulting in a set of beads in which each one contains many cloned copies of the same DNA fragment. A fiber-optic chip filled with a field of microwells, known as a PicoTiterPlate, is then washed with the emulsion, allowing a single bead to drop into each well. The wells are also filled with a set of enzymes for the sequencing process (e.g., DNA polymerase, ATP sulfurylase, and luciferase). At this point, sequencing-by-synthesis can begin, with the addition of bases triggering pyrophosphate release, which produces flashes of light that are recorded to infer the sequence of the DNA fragments in each well as each base type (A, C, G, T) is added.

In another embodiment, the Applied Biosystems SOLiD process (http://solid.appliedbiosystems.com) is used for sequencing of the adaptor ligated nucleic acids. The SOLiD process begins with an emulsion PCR step akin to the one used by 454, but the sequencing itself is entirely different from the previously described systems. Sequencing involves a multiround, staggered, dibase incorporation system. DNA ligase is used for incorporation, making it a "sequencing-by-ligation" approach, as opposed to the "sequencing-by-synthesis" approaches mentioned previously. Mardis (Mardis E R., Next-generation DNA sequencing methods, *Annu Rev Genomics Hum Genet* (2008) 9:387-402) provides a thorough overview of the complex sequencing and decoding processes involved with using this system.

In another embodiment, the Ion Torrent system (http://www.iontorrent.com/) is used for sequencing of the adaptor ligated nucleic acids. The Ion Torrent system begins in a manner similar to 454, with a plate of microwells containing beads to which DNA fragments are attached. It differs from all of the other systems, however, in the manner in which base incorporation is detected. When a base is added to a growing DNA strand, a proton is released, which slightly alters the surrounding pH. Microdetectors sensitive to pH are associated with the wells on the plate, which is itself a semiconductor chip, and they record when these changes occur. As the different bases (A, C, G, T) are washed sequentially through, additions are recorded, allowing the sequence from each well to be inferred.

In another embodiment, the PacBio single-molecule, real-time sequencing approach (http://www.pacificbiosciences.com/) is used for sequencing of the adaptor ligated nucleic acids. The PacBio sequencing system involves no amplification step, setting it apart from the other major next-generation sequencing systems. The sequencing is performed on a chip containing many zero-mode waveguide (ZMW) detectors. DNA polymerases are attached to the ZMW detectors and phospholinked dye-labeled nucleotide incorporation is imaged in real time as DNA strands are synthesized. PacBio's RS II C2 XL currently offers both the greatest read lengths (averaging around 4,600 bases) and the highest number of reads per run (about 47,000). The typical "paired-end" approach is not used with PacBio, since reads are typically long enough that fragments, through CCS, can be covered multiple times without having to sequence from each end independently. Multiplexing with PacBio does not involve an independent read, but rather follows the standard "in-line" barcoding model.

In another embodiment, nanopore sequencing (e.g., as described in Soni, G. V. and Meller A. (2007) *Clin Chem* 53: 1996-2001) is used for sequencing of the adaptor ligated nucleic acids. Nanopore sequencing DNA analysis techniques are being industrially developed by a number of companies, including Oxford Nanopore Technologies (Oxford, United Kingdom), Roche, and Illumina. Nanopore sequencing is a single-molecule sequencing technology whereby a single molecule of DNA is sequenced directly as it passes through a nanopore. Nanopore sequencing is an example of direct nucleotide interrogation sequencing, whereby the sequencing process directly detects the bases of a nucleic acid strand as the strand passes through a detector. A nanopore is a small hole, of the order of 1 nanometer in diameter Immersion of a nanopore in a conducting fluid and application of a potential (voltage) across it results in a slight electrical current due to conduction of ions through the nanopore. The amount of current which flows is sensitive to the size and shape of the nanopore. As a DNA molecule passes through a nanopore, each nucleotide on the DNA molecule obstructs the nanopore to a different degree, changing the magnitude of the current through the nanopore in different degrees. Thus, this change in the current as the DNA molecule passes through the nanopore represents a reading of the DNA sequence. Another example of direct nucleotide interrogation sequencing that may be used in conjunction with the present methods is that of Halcyon.

Kits

Kits are provided for practice of the methods described herein by an end user, i.e., for preparation of adaptor ligated nucleic acids, e.g., in nucleic acid libraries, such as, but not limited to, nucleic acid libraries for sequencing.

In some embodiments, a kit is provided that includes any of the adaptors described herein, supra. For example, the kit may include nucleic acid adaptors that include a first nucleic acid strand with a first 5' end and a first 3' end and a second nucleic acid strand with a second 5' end and a second 3' end, wherein each adaptor includes a double stranded region, e.g., a double stranded region that includes the first 3' end, a first single stranded region including the first 5' end, and a second single stranded region including the second 3' end, and wherein the second 3' end includes a modification to prevent extension with a DNA polymerase enzyme. Optionally, the adaptors may include a 5' overhang sequence that includes the 5' end, a modification at or near the first 3' end to prevent degradation by an exonuclease enzyme, and/or a modification at the first 5' end to prevent phosphorylation and ligation. In some embodiments, the double stranded region of the adaptors is blunt ended and is either phosphorylated or unphosphorylated at the 5' terminal nucleotide of the double stranded region. In various embodiments, a kit may include adaptors with any of the configurations described herein.

In some embodiments, a kit further includes one or more enzyme(s) for preparation of a nucleic acid library as described herein. For example, the kit may include a proofreading DNA polymerase enzyme, a polynucleotide kinase enzyme, and/or a ligase enzyme, all of which are capable of enzymatic activity at the same temperature. Optionally, the kit may also include buffers, co-factors, etc. that are necessary for activity of the enzymes in a method for nucleic acid library preparation as described herein.

A kit may be provided in suitable packaging. As used herein, "packaging" refers to a solid matrix or material customarily used in a system and capable of holding within fixed limits a composition suitable for use in a method as described herein. Such materials include glass and plastic (e.g., polyethylene, polypropylene, and polycarbonate) bottles, vials, paper, plastic, and plastic-foil laminated envelopes and the like. If e-beam sterilization techniques are employed, the packaging should have sufficiently low density to permit sterilization of the contents.

A kit may further include instructions for use in a method for preparation of a nucleic acid library as disclosed herein. For example, instructions may be provided in printed form or in the form of an electronic medium such as a CD or DVD, or in the form of an Internet link or website address where such instructions may be obtained.

Reaction Mixtures

Reaction mixtures are provided for practice of the methods described herein, i.e., for preparation of adaptor ligated nucleic acids, e.g., in nucleic acid libraries, such as, but not limited to, nucleic acid libraries for sequencing.

A reaction mixture may include any of the adaptors described herein, supra. For example, the reaction mixture may include nucleic acid adaptors that include a first nucleic acid strand with a first 5' end and a first 3' end and a second nucleic acid strand with a second 5' end and a second 3' end, wherein each adaptor includes a double stranded region, e.g., a double stranded region that includes the first 3' end, a first single stranded region including the first 5' end, and a second single stranded region including the second 3' end, and wherein the second 3' end includes a modification to prevent extension with a DNA polymerase enzyme. Optionally, the adaptors may include a 5' overhang sequence that includes the 5' end, a modification at or near the first 3' end to prevent degradation by an exonuclease enzyme, and/or a modification at the first 5' end to prevent phosphorylation and ligation. In some embodiments, the double stranded region of the adaptors is blunt ended and is either phosphorylated or unphosphorylated at the 5' terminal nucleotide of the double stranded region.

A reaction mixture includes a proofreading DNA polymerase enzyme, a polynucleotide kinase enzyme, and/or a ligase enzyme, all of which are capable of enzymatic activity at the same temperature. The reaction mixture may also include buffers, co-factors, etc. that are necessary for activity of the enzymes in a method for nucleic acid library preparation as described herein A reaction mixture is maintained at a temperature that is suitable for enzymatic activity of the enzymes in a method for nucleic acid library preparation as described herein, e.g., a single temperature at which the proofreading DNA polymerase, the polynucleotide kinase, and the ligase enzyme in the reaction mixture are all enzymatically active and capable of performing the enzymatic activities described herein for preparation of a nucleic acid library. In some embodiments, the temperature of the reaction mixture is about 16° C. to about 37° C. In one embodiment, the temperature is room temperature, e.g., about 20° C. to about 25° C.

A reaction mixture may also include sample nucleic acids or amplified sample nucleic acids, as described herein, for example, cell-free DNA, fragmented portions of genomic DNA, or cDNA transcribed from cellular RNA, or nucleic acids from any biological sample or source as described herein, supra.

The following examples are intended to illustrate, but not limit, the invention.

EXAMPLES

Example 1

Approximately 6 ng of cell-free DNA (cfDNA) (170 bp subunits) was mixed with "AIOLP mastermix" (a 4× mixture that contained buffers, salts, deoxynucleotides, and enzymes (DNA polymerase, polynucleotide kinase, and DNA ligase)), and adaptors as shown in FIG. 1A.

The adaptors each contained a top strand and a bottom strand. The 5' end of the top strand contained a 5' carbon spacer, and the last three bases at the 3' end of the top strand contained a phosphorothioate modification. The adaptors contained a 5' overhang from the bottom strand, and the 3' end of the bottom strand contained an inverted dT.

40 µl of cfDNA at a concentration of 0.15 ng/µl was combined with 15 µl of the AIOLP mastermix and 5 µl of 0.8 µM adaptors. The reaction mixture was incubated at room temperature for 15 minutes, followed by an SPRI bead cleanup to purify the reaction products.

Twelve cycles of PCR were performed using the KAPA HiFi PCR system (http://www.biocompare.com/21262-PCR-Kits/7370230-KAPA-HiFi-PCR-Kit-with-dNTPs/).

The final yield of the library, after PCR, was approximately 1.1 mg.

Figure 4:
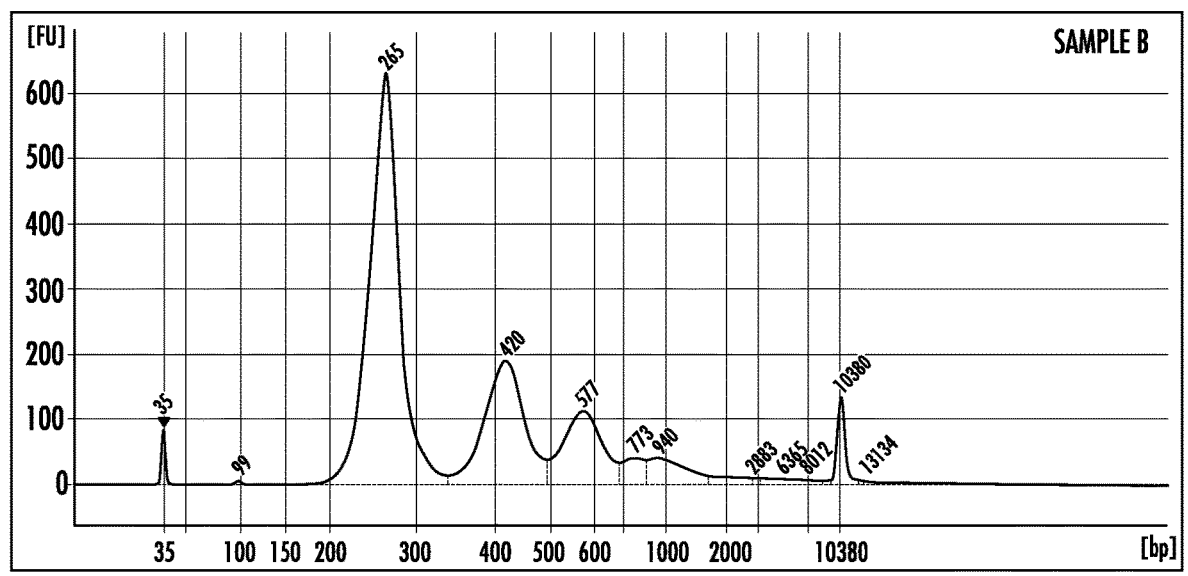
FIG. 4 shows the results of the experiment described in Example 1.

The results are shown in FIG. 4. FIG. 4 is a bioanalyzer trace of the PCR amplified adaptor ligated cfDNA. The size nature of the cfDNA size is in units of 170 bp, with the highest fraction at 170 bp, then 340 bp, then 510 bp, etc. Each adaptor adds 46 base pairs. The adaptor ligated library should contain an adaptor ligated to each side of the original duplex, hence adding a total of 92 base pairs. Each major peak of the bioanalyzer trace shows an addition of 92 base pairs, which indicates a successful library creation.

Although the foregoing invention has been described in some detail by way of illustration and examples for purposes of clarity of understanding, it will be apparent to those skilled in the art that certain changes and modifications may be practiced without departing from the spirit and scope of the invention. Therefore, the description should not be construed as limiting the scope of the invention, which is delineated in the appended claims.

All publications, patents, and patent applications cited herein are hereby incorporated by reference in their entireties for all purposes and to the same extent as if each individual publication, patent, or patent application were specifically and individually indicated to be so incorporated by reference.

We claim:

1. A method for preparing a nucleic acid library, comprising:
   (a) contacting a plurality of DNA duplex fragments comprising first and second nucleic acid strands with a reaction mixture that comprises:
   (i) nucleic acid adaptors, wherein each adaptor comprises a first nucleic acid strand comprising a first 5' end and a first 3' end and a second nucleic acid strand comprising a second 5' end and a second 3' end, wherein each adaptor comprises a double stranded region, a first single stranded region comprising the first 5' end, and a second single stranded region comprising the second 3' end,
   wherein the second 3' end comprises a modification selected from a carbon spacer, a dideoxynucleotide base, or an inverted deoxynucleotide base, to prevent extension with a DNA polymerase enzyme and degradation by an exonuclease;
   (ii) a proofreading DNA polymerase enzyme,
   wherein the proofreading DNA polymerase enzyme degrades 3' overhang sequences, if any, and fills in 5' overhang sequences, if any, on the DNA duplex fragments and/or on the nucleic acid adaptors, thereby producing blunt ended DNA duplex fragments comprising first and second ends, wherein each of the first and second strands of the DNA duplex comprises a 5' terminal nucleotide and/or wherein the proofreading DNA polymerase enzyme degrades 3' overhang sequences, if any, and fills in 5' overhang sequences, if any, on the adaptors, producing adaptors with blunt ended double stranded regions comprising 5' terminal nucleotides;
   (iii) a polynucleotide kinase enzyme that phosphorylates the 5' terminal nucleotides on the first and second strands of said DNA duplex fragments and/or on the double stranded regions of the adaptors; and
   (iv) a ligase enzyme that joins said adaptor double stranded regions to each of the first and second ends of the DNA duplex fragments, thereby producing adaptor ligated DNA duplex fragments; and
   (b) incubating the reaction mixture between about 10 and 20 minutes at a temperature at which the proofreading DNA polymerase enzyme, the polynucleotide kinase enzyme, and the ligase enzyme are enzymatically active,
   thereby preparing a nucleic acid library comprising adaptor ligated DNA duplex fragments.

2. A method according to claim 1, wherein each adaptor comprises a 5' overhang comprising the second 5' end,
   wherein the proofreading DNA polymerase enzyme fills in the 5' overhang sequences of the double stranded regions of the adaptors, thereby producing blunt ended adaptor duplex regions,
   wherein the blunt ended adaptor duplex region comprises a 5' terminal nucleotide, and
   wherein the polynucleotide kinase enzyme phosphorylates the 5' terminal nucleotide of the adaptor duplex.

3. A method according to claim 1, wherein the double stranded region of each adaptor is blunt ended and comprises:
   a 5' terminal phosphate: or
   a 5' terminal nucleotide, wherein the polynucleotide kinase enzyme phosphorylates the 5' terminal nucleotide of the adaptor double stranded region.

4. A method according to claim 1, wherein the first 3' ends of the adaptors comprise a modification at or near the first 3' ends to prevent degradation by an exonuclease enzyme.

5. A method according to claim 1, wherein the first 5' ends of the adaptors comprise a modification to prevent phosphorylation and ligation.

6. A method according to claim 1, wherein the adaptors further comprise:
   a modification at the first 3' end to prevent degradation by an exonuclease enzyme; and
   a modification at the first 5' end to prevent phosphorylation and ligation; and a 5' overhang comprising the second 5' end,
   wherein the proofreading DNA polymerase enzyme fills in the 5' overhang sequences of the double stranded regions of the adaptors, thereby producing blunt ended adaptor duplex regions, wherein the blunt ended adaptor duplex region comprises a 5' terminal nucleotide, and wherein the polynucleotide kinase enzyme phosphorylates the 5' terminal nucleotide of the adaptor duplex.

7. A method according to claim 1, further comprising amplifying the adaptor ligated DNA duplex fragments produced in step (b).

8. A method according to claim 1, wherein the DNA duplex fragments comprise cell-free DNA, fragmented portions of genomic DNA, or fragments comprising cDNA transcribed from cellular RNA of a biological sample.

9. A method according to claim 1, further comprising obtaining the DNA duplex fragments from DNA or RNA from a biological sample prior to step (a).

10. A method according to claim 1, further comprising amplifying DNA or RNA sequences from a biological sample prior to step (a).

11. A method according to claim 1, wherein the adaptors comprise a sample index sequence, a flow cell binding sequence, and/or a sample or source specific barcode sequence.

12. A method for nucleic acid sequencing, comprising preparing a nucleic acid library comprising adaptor ligated DNA duplex fragments according to claim 1; and sequencing the adaptor ligated DNA duplex fragments, optionally wherein the adaptor ligated DNA duplex fragments are amplified prior to sequencing.

* * * * *